United States Patent [19]

Martin

[11] Patent Number: 5,334,148
[45] Date of Patent: Aug. 2, 1994

[54] BALLOON CATHETER

[75] Inventor: Geoffrey S. Martin, Mississauga, Canada

[73] Assignee: Med-Pro Design, Inc., Mississauga, Canada

[21] Appl. No.: 995,216

[22] Filed: Dec. 22, 1992

[30] Foreign Application Priority Data

Jan. 30, 1992 [CA] Canada .................................. 2060133

[51] Int. Cl.$^5$ ............................................. A61M 29/00
[52] U.S. Cl. ...................................... 604/96; 606/194
[58] Field of Search ................................ 604/96–101; 606/192–195

[56] References Cited

U.S. PATENT DOCUMENTS

| 4,771,776 | 9/1988 | Powell et al. | 128/344 |
| 4,782,834 | 11/1988 | Maguire et al. | 604/96 |
| 4,838,268 | 6/1989 | Keith et al. | 128/344 |
| 4,958,634 | 9/1990 | Jang | 604/194 |
| 4,976,690 | 11/1990 | Solar et al. | 604/96 |
| 5,015,230 | 5/1991 | Martin et al. | 604/96 |
| 5,078,727 | 1/1992 | Hannam et al. | 606/194 |

FOREIGN PATENT DOCUMENTS 8911306 11/1989 PCT Int'l Appl. ......... A61M 25/00

OTHER PUBLICATIONS

Webster's New Collegiate Dictionary, Springfield, Mass., 1973 "elastic".

Primary Examiner—Jerome L. Kruter
Attorney, Agent, or Firm—Rogers & Scott

[57] ABSTRACT

An angioplasty catheter is provided having a main body defining a first lumen for receiving a guide wire and a second lumen terminating at an opening inside the balloon for inflating and deflating the balloon. A tubular section extends from the main body through the balloon and terminates at a catheter to form an extension of the first lumen, and the tubular section includes a tip portion extending from within the balloon to the catheter tip. The tip portion is sufficiently flexible and elastic to permit the inflated balloon to follow the shape and contours of blood vessels in which the catheter is inserted for use.

7 Claims, 2 Drawing Sheets

BALLOON CATHETER

This invention relates to balloon catheters for use in angioplasty procedures and in particular to such catheters which are advanced along a guide wire to a location where a stenosis is to be expanded radially outwardly using the balloon.

A large number of balloon catheters have been devised for angioplasty procedures. Commonly a guide wire is first introduced percutaneously into the patient's vascular system and advanced and steered to the site of a stenosis. A balloon or dilation catheter is then advanced over the guide wire until the balloon is positioned within the stenosis so that on inflation, the balloon will compress the stenosis by dilatation of the artery to thereby re-establish a more adequate blood flow path past the stenosis.

Various forms of guide wires have been developed which can be steered along blood vessels to negotiate the many twists and turns and branches to be found in these vessels. The wire is extremely flexible but in its relaxed state it often is made to have a J-shaped end. Consequently, as the wire moves along a blood vessel, the wire can be rotated to align the end of the wire as required to enter branches and to negotiate irregularities.

Once the wire is in a selected position, the catheter is then pushed over the wire until the balloon is located in the stenosis ready for dilatation. There are of course many criteria that the balloon catheter must meet. The first is that it should be very small and the balloon is conventionally wrapped around the catheter in a tight configuration where it remains until it is inflated. Also there must be sufficient flexibility in the catheter to manipulate the catheter along the wire. This can lead to some difficulty because the material must have sufficient strength to be pushed along the wire while at the same time be flexible enough not to damage the blood vessels as it passes through them. These conflicting requirements lead to some difficulty with the structure. However there is a further difficulty because when the balloon is inflated, there is a tendency for the strength of the catheter to maintain the balloon in at straight condition and this in itself is not desirable because the balloon may have to be located in a curved section of a blood vessel in order to expand the stenosis.

Attempts have been made to meet some of the requirements. For instance, U.S. Pat. No. 4,976,690 to R. J. Solar et al provides for a balloon attached to the main body of the catheter by way of a flexible portion which enhances the flexibility of the catheter as it is being pushed over the wire. This does not meet the problem of inflation resulting in a straight balloon because the flexibility is lost once the balloon is inflated.

It is an object of the present invention to provide a catheter which has sufficent inherent flexibility to permit the catheter to follow a guide wire through irregular and tortuous paths in blood vessels, and also to permit the balloon to inflate and follow the general shape of the vessel where the stenosis is to be compressed by dilatation.

In one of its aspects the invention provides a balloon catheter of the type used in angioplasty and having a main body defining a first lumen for receiving a guide wire and a second lumen terminating at an opening inside the balloon for inflating and deflating the balloon. A tubular section extends from the main body through the balloon and terminates at a catheter tip to form an extension of the first lumen. The tubular section includes a tip portion extending from within the balloon to the catheter tip and the tip portion is sufficiently flexible and elastic to permit the inflated balloon to follow the shape and contours of blood vessels in which the catheter is inserted for use.

This and other aspects of the invention will be better understood with reference to the drawings, in which.

Figure 1:
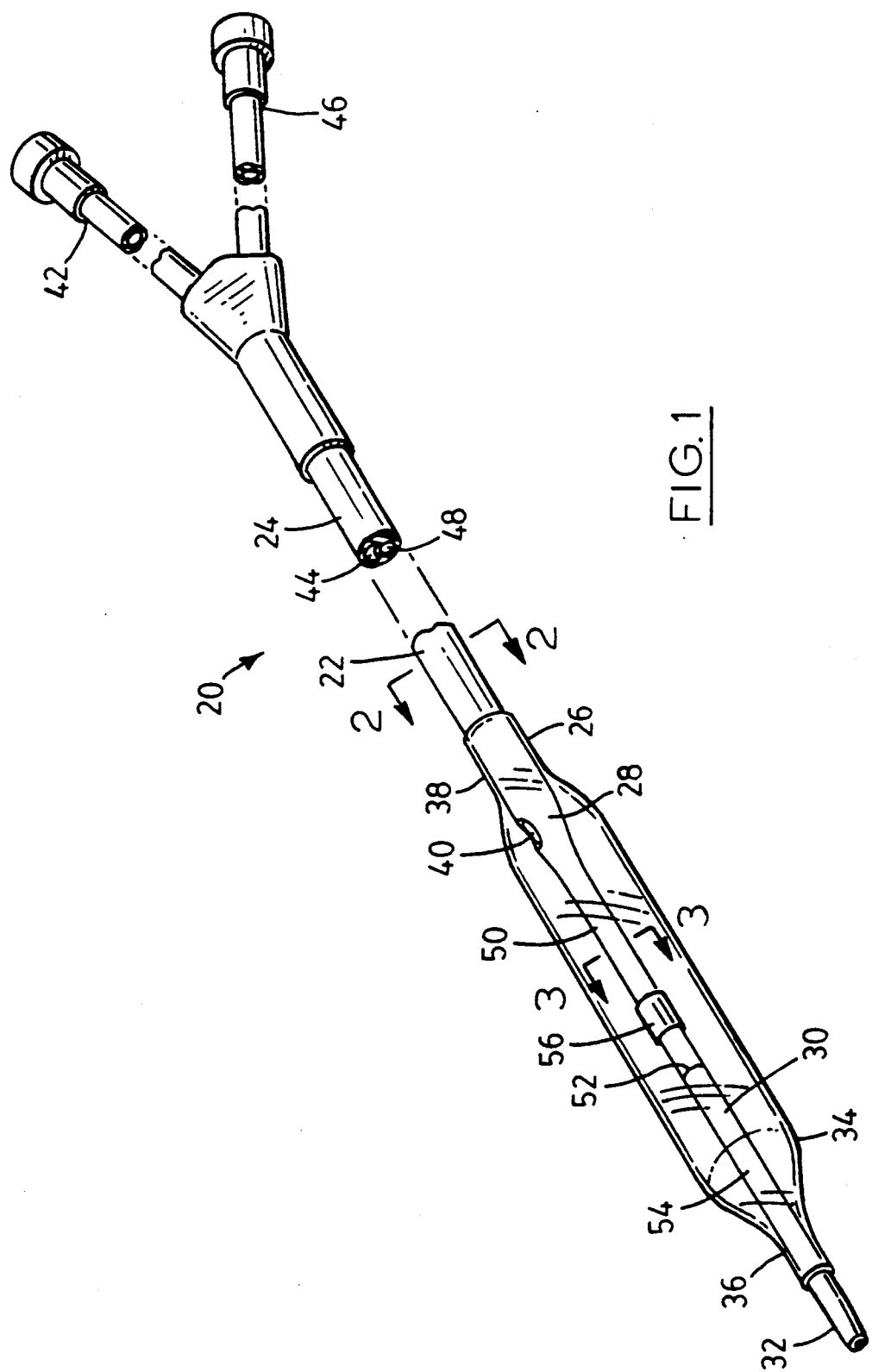
FIG. 1 is a perspective view of a preferred embodiment of a catheter according to the invention and drawn to an enlarged scale portions broken away to better illustrate details of the construction.

Reference is first made to FIG. 1 which illustrates an angioplasty catheter designated generally by the numeral 20 and having a main body 22 extending from a proximal end 24 to a distal end 26. At the distal end the body meets a transition portion 28 and a tip section 30 extends from the transition portion 28 to a tip 32. A balloon 34 is shown in the inflated condition and contains part of the tip section 30 extending between a first end 36 of the balloon and a second end 38. The balloon is inelastic so that when inflated it will maintain the generally cylindrical shape shown in FIG. 1. Prior to inflation it will be wrapped around the tip section 30 in what has become conventional fashion.

The second end 38 of the balloon is attached to the main body 22 so that an opening 40 in the circumference of the main body at the transition portion 28 is inside the balloon 34 for inflating the balloon by applying pressure to a connection 42 communicating with an inflation lumen 44 ending at the opening 40. A second connection 46 at the proximal end provides access for a wire (not shown in FIG. 1) which passes through the connection 46, through a lumen 48 and, through the tip section 30 which forms an extension of the lumen 48 as will be explained.

Figure 2:
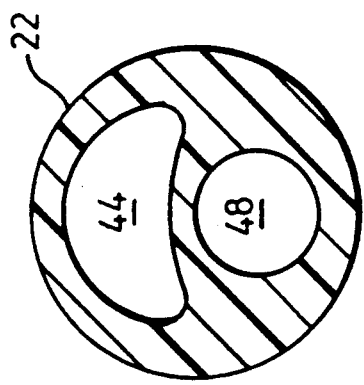
FIG. 2 is a sectional view on line 2—2 of FIG. 1 and drawn to a larger scale than FIG. 1.
Figure 3:
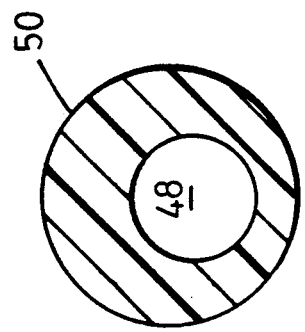
FIG. 3 is a view similar to FIG. 2 and drawn on line 3—3 of FIG. 1.

As seen in FIG. 2, the section of the main body at line 2—2 of FIG. 1 shows the first or guide wire lumen 48 to be round and offset from the centre of the main body 22. This allows for the inclusion of a generally C-shaped second or inflation lumen 44 of a size which will permit quick inflation and deflation of the balloon 34. The cross-section in FIG. 2 is modified at the tip section 30 by applying heat and pressure to collapse the section shown in FIG. 2 about a mandrel placed in the lumen 48. The result is a section such as that shown in FIG. 3 where the lumen 48 remains patent and the remainder of the material has been merged into a solid to close off the lumen 44 shown in FIG. 2. This transition from the cross-section at FIG. 2 to the cross-section at FIG. 3 takes place at the transition portion 28 where the opening 40 is formed to provide access to the second lumen 44 within the balloon 34.

Returning to FIG. 1, the tip section 30 is in two parts. First of all an intermediate portion 50 is preferably formed integrally from the material of the main body 22 by deformation as described with reference to the cross-section shown in FIG. 3. This intermediate portion ends at a joint 52 preferably located at about half the length of the balloon. The portion 50 is bonded at the joint to a tip portion 54 forming an extension of the portion 50 to accommodate a guide wire as will be described. This tip section terminates at the end opening 32 and is of a material significantly more flexible and elastic than the material forming the main body and intermediate portion 50. The purpose of this will be described more fully with reference to FIG. 4.

As mentioned earlier, the balloon 34 is attached at its ends and it contains a radiopaque sleeve 56 for identification and location during the surgical procedure.

It will be appreciated that the drawings are to a scale which enlarges the structure significantly. The actual product is about 2 French with the tip portion 54 being in the order of 1.8 French. The balloon is a filmic material and will have minimal effect on the outer profile where it is joined to the main body at 38 and to the tip section at 36. For the sake of being able to show these parts in a drawing, the filmic balloon is given a significant thickness to show where it fits. These thicknesses are purely for the sake of illustrating the invention and in practice the sizes are so small that the ends of the balloon would not be apparent.

Figure 4:
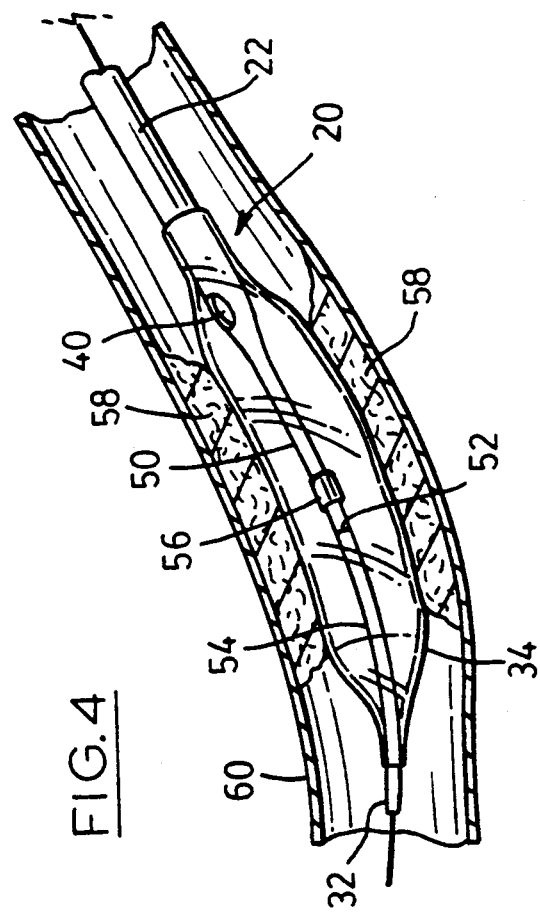
FIG. 4 is a diagrammatic sectional view showing the catheter balloon during dilatation inside a curved blood vessel.

Reference is now made to FIG. 4 which is a diagrammatic representation of the use of the catheter 20 to compress a stenosis 58 by dilatation of the containing blood vessel 60. As can be seen this particular section of vessel is curved and the balloon is tending to follow this curvature due to the fact that the tip section 54 provides minimal control over the shape of the balloon but rather deflects under the influence of the stenosis on the balloon. As a result of this, the curvature of the blood vessel in effect controls the shape of the balloon and consequently the radial forces applied to compress the stenosis are applied as evenly as possible to give overall compression of the stenosis with smooth transitions along the path of the blood vessel.

The kind of location demonstrated in FIG. 4 is quite typical. In many intances the curvature of the blood vessel is significantly more acute than shown in FIG. 4 in which case it would not be surprising if the tip section were in contact with the wall of the vessel. Because of its great flexibility, it is possible for this to take place without damaging the vessel.

It should also be noted that the tip portion 54 is somewhat elastic. It is therefore capable of expanding in length under the influence of the inflated balloon. This again helps to permit the balloon to take up the position it prefers in the blood vessel.

In the preferred embodiment, the main body is of a polyether polyamide co-polymer and the tip section is of a grade and size of the same material selected to be much more flexible than the main body and to have some elasticity compared with the main body 22. These co-polymers are compatible with, and can be used with, suitable grades of polyamides. In general, the desired physical characteristics are those described, and materials suitable for medical use and designed with these characteristics would also be suitable.

It will be appreciated that the catheter can be made in a number of various ways equivalent to that described. For instance, the intermediate portion 50 could be a separate piece attached to the main body by first flaring an end over the distal end of the main body and then deforming the connection under the influence of heat and pressure to create the transition portion 28. Such structures, are within the scope of the invention.

I claim:

1. A balloon catheter for use in angioplasty at a selected location in a blood vessel, the catheter comprising:

a co-axial balloon;

an elongate main body defining first and second lumens and extending axially between proximal and distal ends;

first and second connections attached to the proximal ends of the main body in fluid communication with respective ones of the first and second lumens;

an intermediate portion extending axially from the distal end of the main body and forming a continuation of the first lumen;

an opening through the circumference of said intermediate portion providing communication with the second lumen;

tip portion means attached to the intermediate portion within said balloon and extending axially to form a further extension of the first lumen and defining an end opening so that the first lumen can accommodate a guide wire through the end opening and said first connection;

said co-axial balloon being attached to the main body and to the tip section to contain said opening in the intermediate portion for inflating and deflating the balloon; and said tip portion means being more flexible and elastic than the intermediate portion such that the tip portion will readily deflect transversely as the balloon is inflated to permit the balloon to take up the shape of the blood vessel at said selected location.

2. A catheter as claimed in claim 1 in which the intermediate portion is attached to the tip portion at about the med-point of the axial length of the balloon.

3. A catheter as claimed in claim 1 in which the first lumen is circular in cross-section and in which the second lumen is generally C-shaped in cross-section.

4. A catheter as claimed in claim 1 and further comprising a transition portion where the main body meets the intermediate portion, the second lumen being closed at the transition portion by collapsing the second lumen and said opening in the intermediate portion being adjacent the transition portion.

5. A catheter as claimed in claim 4 in which the main portion, transition portion and intermediate portion are integral.

6. A catheter as claimed in claim 5 in which the tip portion is bonded to the intermediate portion.

7. A balloon catheter as claimed in claim 1 in which the main body and intermediate portion are of a first thermoplastic synthetic material of sufficient rigidity to permit pushing the catheter over a guide wire in the first lumen, and in which the tip portion is of a second material having significantly more flexibility and elasticity than said first material.

* * * * *